United States Patent [19]
Chupp et al.

[11] Patent Number: 5,631,730
[45] Date of Patent: May 20, 1997

[54] PSEUDO TELECENTRIC OPTICAL DESIGN FOR FLOW CYTOMETRIC BLOOD CELL ANALYZER

[75] Inventors: Vernon L. Chupp, Los Altos; Suresh N. Mehta, Pleasanton, both of Calif.

[73] Assignee: Abbott Laboratories, Abbott Park, Ill.

[21] Appl. No.: 508,502

[22] Filed: Jul. 28, 1995

Related U.S. Application Data

[63] Continuation-in-part of Ser. No. 283,379, Aug. 1, 1994, Ser. No. 482,678, Jun. 7, 1995, and Ser. No. 488,532, Jun. 7, 1995.

[51] Int. Cl.$^6$ .................................................. G01N 21/53
[52] U.S. Cl. ............................................ 356/73; 356/339
[58] Field of Search .................................. 356/72, 73, 339, 356/338

[56] References Cited

U.S. PATENT DOCUMENTS

| | | |
|---|---|---|
| 4,038,556 | 7/1977 | Auer et al. . |
| 4,953,979 | 9/1990 | Hirako ................................ 356/338 |
| 4,989,977 | 2/1991 | North, Jr. . |
| 5,135,302 | 8/1992 | Hirako . |

OTHER PUBLICATIONS

Jacobs, Donald H. "Fundamentals of Optical Engineering", first edition, 1943. McGraw–Hill Book Company, Inc. pp. 52–53.

Primary Examiner—Richard A. Rosenberger
Attorney, Agent, or Firm—Mark C. Bach

[57] ABSTRACT

A pseudo telecentric flow cytometric optical system for the simultaneous detection of several characteristics of particles suspended in a flowing medium. The system is made up of a flowcell through which the particles pass substantially one particle at a time, an optical system for directing light from a light source onto the flowing particles in the flowcell, a side angle optical collection system for receiving light from the flowing particles and for directing the light to one or more of a first set of detectors, and a forward angle collection system for receiving light from the flowing particles and for directing the light to one or more of a second set of detectors. The side angle optical collection system can include a condenser lens for directing light toward the first set of detectors with an exit pupil of the condenser lens located at the back focal plane of the condenser lens; a photosensitive surface of one or more of the first set of detectors is located at conjugate points of the back focal plane of the condenser lens such that an image of the exit pupil is positioned at the photosensitive surface of one or more of the first set of detectors. The forward angle optical collection system can include a collecting lens for directing light toward the second set of detectors where the collecting lens exit pupil is located in the back focal plane of the collecting lens and a photosensitive surface of one or more of the second set of detectors is located at the back focal plane of the collecting lens.

34 Claims, 4 Drawing Sheets

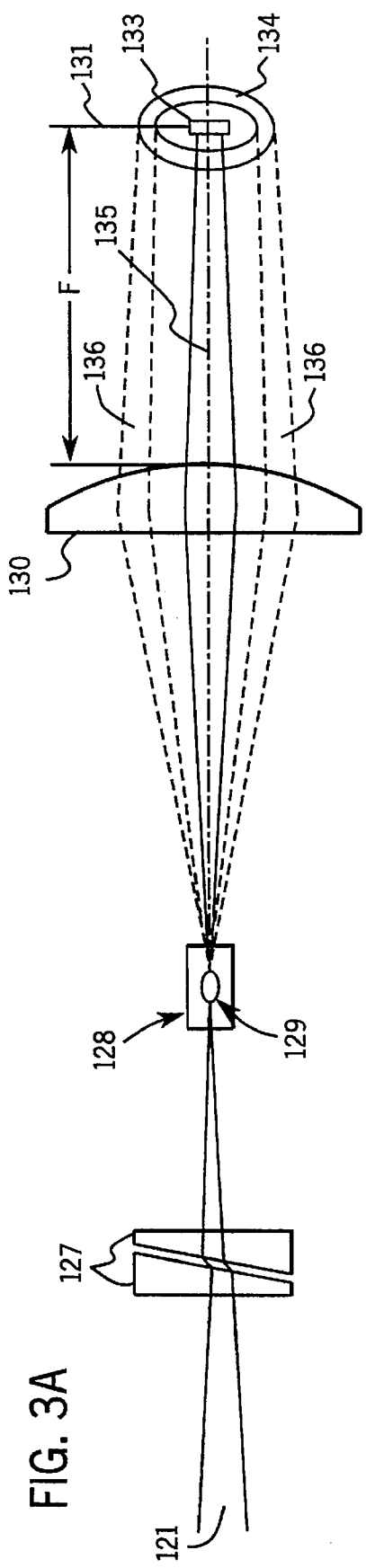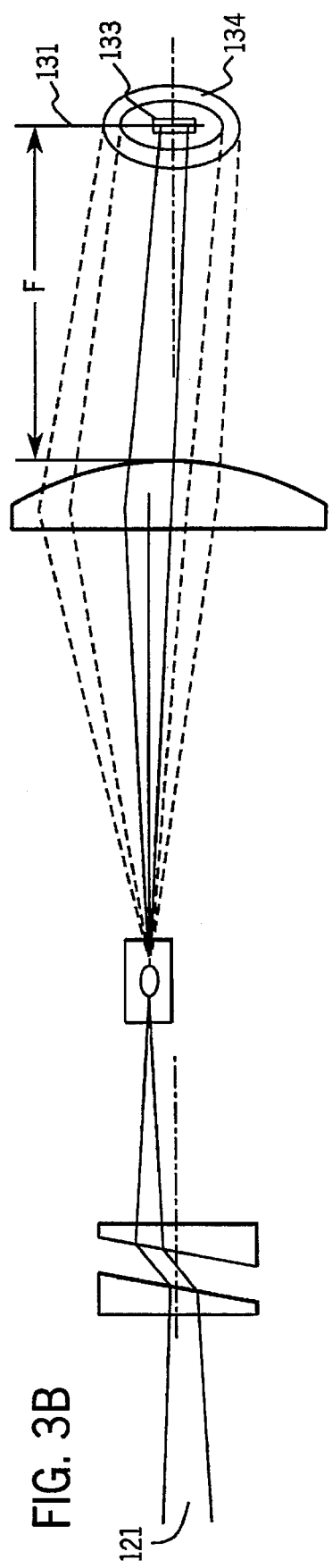
FIG. 3A
FIG. 3B

PSEUDO TELECENTRIC OPTICAL DESIGN FOR FLOW CYTOMETRIC BLOOD CELL ANALYZER

This is a continuation-in-part application of: Ser. No. 08/283,379, filed Aug. 1, 1994; Ser. No. 08/482,678, filed Jun. 7, 1995; and Ser. No. 08/488,532, filed Jun. 7, 1995, all entitled "Method And Apparatus For Performing Automated Analysis". The parent applications are assigned to the assignee of this application. The disclosures of the parent applications are incorporated herein in their entirety by this reference.

BACKGROUND OF THE INVENTION

This invention relates to a multi-dimensional optical design. More particularly the invention relates to an optical design of a multi-dimensional system which can simultaneously detect five or more distinct properties of particles or cells when the design is applied to a flow cytometric analyzer.

Particle analysis, known generally as flow cytometry, consists of passing particles one at a time through a sensing region of a flowcell, and detecting the properties or characteristics, of each particle. These specific properties, which are sometimes referred to as dimensions, are usually combinations of multi-angle light scatter and multi-color fluorescence.

Flow cytometry has become a particularly important method for analyzing blood cells in the hematology laboratory where patient test load is an important metric. This is because the method is rapid, enabling as many as five to ten thousand cells per second to be analyzed, and because it is much more statistically accurate than the manual microscope inspection method. It is important, however, to the hematology laboratory, that the entire process, both sample preparation and analysis, be automated.

A large number of products exist today which feature such multi-dimensional capability, but only a few automate the entire process. Two of the most well known such products in which the entire process of blood cell analysis, or differentiation is fully automated are the Cell-Dyn® series 3000 and 3500 analyzers manufactured by Abbott Diagnostics. Each of these instruments measures simultaneously four dimensions which include three angles of laser light scatter, and a fourth dimension which is depolarized light scatter.

A number of products exist which measure several simultaneous dimensions of fluorescence and scatter in which only the analysis is automated. One of the most well known of these is the Becton Dickinson FACScan® flow cytometer. This instrument is capable of simultaneously detecting one dimension of forward scatter, one dimension of side scatter, and three colors of fluorescence.

However, in none of these multi-dimensional products which combine several colors of fluorescence and light scatter, is the entire process automated. Part of the reason for this is the complexity of building a system which is stable enough to maintain proper alignment for many simultaneous dimensions while at the same time, assuring the measurement integrity of each cell or particle in the sample stream for all dimensions.

Among the prior art contributions, is the Auer et al. U.S. Pat. No. 4,038,556 which describes a two-dimensional system with a flowcell, a laser light source, and two simultaneous optical paths, a side angle collection system for measuring cell fluorescence, and a forward angle system for measuring light scatter. The patent teaches that by placing the forward angle detector in the back focus of a light collecting lens, an important and practical simplification of system alignment results; the precise relationship of the forward angle optical system, with respect to the remaining elements of the system, is greatly relaxed. Although the side angle beam focus, the laser beam focus, and the stream focus must be established to be mutually collinear in the Auer et al. teachings, it is not required for the forward angle path. This is due to design of the forward path system which transforms the two dimensional distribution of intensity vs angular distribution in the flowcell space to intensity vs spatial distribution at the detector.

Hirako, in U.S. Pat. No. 4,953,979, describes a side angle collection system for flow cytometry which has the PMT front surface conjugate with the condenser exit pupil while the flow stream (containing the particles or cells) is conjugate with an external aperture located between the condenser and the PMT. The external aperture, which limits unwanted background light, is located at the front focus of a second lens, which functions to image the condenser exit pupil on the PMT. The patent teaches that as the stream position, or cell position within the stream varies, the effect on cell coefficient of variant ("C.V.") of detector sensitivity variations are eliminated.

Hirako, ignores the C.V. effect of stream or cell position variations within the flowcell upon the angular integrity of the scattered light with respect to the laser beam.

It is one object of this invention to maintain the angular integrity of the scattered light with respect to the laser beam in both the forward and side angle light paths.

It is another object of this invention to improve the stability of, and at the same time simplify, the alignment and tracking requirements of a multi-dimensional flow cytometer.

It is yet another object of this invention to combine this design approach with a multi-element array detector and a simple laser beam translating mechanism, to assure beam to stream tracking simplification, while at the same time assuring the measurement integrity of each particle or cell, independent of cell location in the stream, or the precise stream location within the flowcell.

It is another object of this invention to maximize these advantages in at least two separate light paths simultaneously.

These and other advantages will become more apparent in the following detailed description.

SUMMARY OF THE INVENTION

The present invention is directed to a flow cytometric optical system for the simultaneous detection of several characteristics of particles suspended in a flowing medium wherein the system comprises a flowcell through which the particles pass substantially one particle at a time, an optical system for directing light from a light source onto the flowing particles in the flowcell, a side angle optical collection system for receiving light from the flowing particles and for directing the light to one or more of a first set of detectors, and a forward angle collection system for receiving light from the flowing particles and for directing the light to one or more of a second set of detectors. The side angle optical collection system comprises a condenser lens for directing light toward the first set of detectors with an exit pupil of the condenser lens located at the back focal plane of the condenser lens; a photosensitive surface of one or more of the first set of detectors is located at conjugate points of the back focal plane of the condenser lens such that an image of the exit pupil is positioned at the photosensitive surface of one or more of the first set of detectors. The forward angle optical collection system comprises a collecting lens for directing light toward the second set of detectors where the collecting lens exit pupil is located in the back focal plane of the collecting lens and a photosensitive surface of one or more of the second set of detectors is located at the back focal plane of the collecting lens.

BRIEF DESCRIPTION OF THE DRAWINGS

FIGS. 3a and 3b are a schematic of a forward scatter optics system of a preferred embodiment of the present invention.

DETAILED DESCRIPTION OF THE INVENTION

Although geometric imaging doesn't have the same significance in a flow cytometer system as in a diffraction limited system such as an optical microscope, the performance of a flow cytometer system is best understood by means of simple geometric image analysis.

Figure 1:
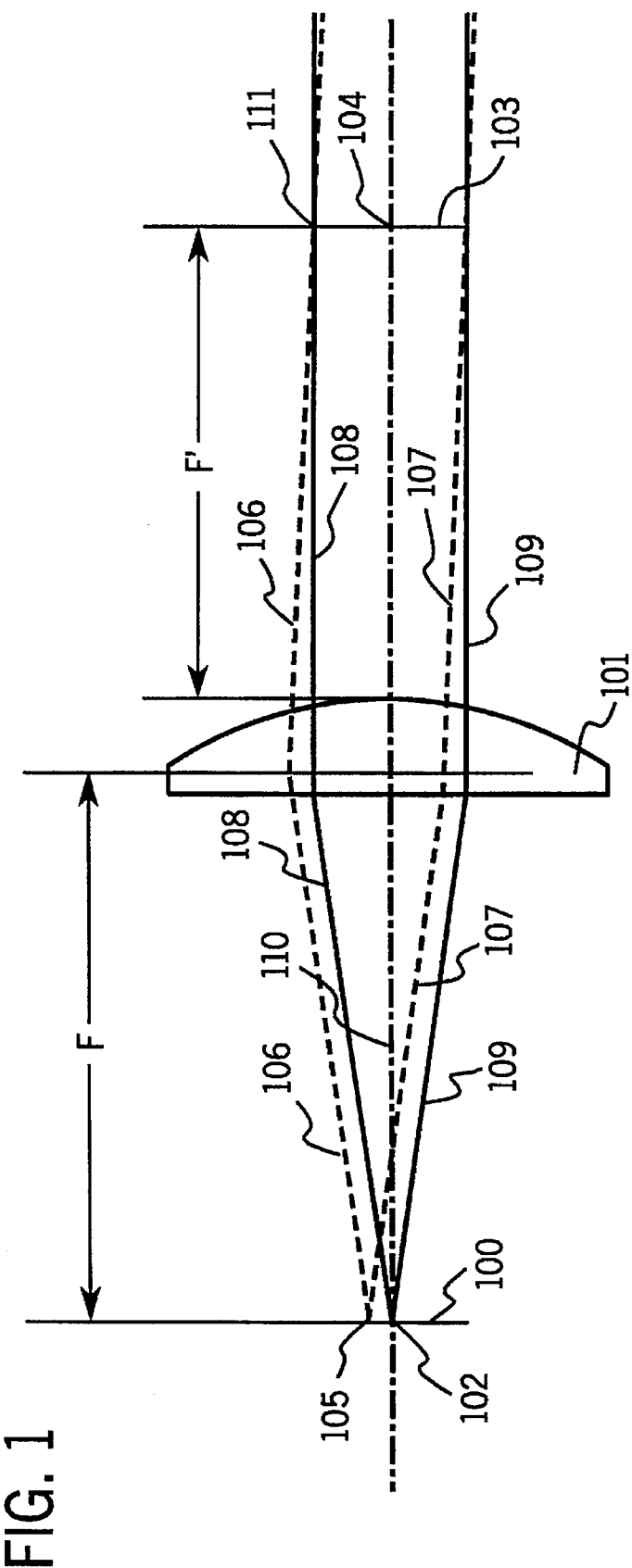
FIG. 1 is a schematic of the optics of a simple microscope.

In all properly designed systems, there are two system stops which function to limit the ray paths through the system. At any point along the optical path, these stops, or images of these stops, determine the extreme ray paths which are admitted through the system. In classical geometric optics, the one stop can be referred to the "field" stop, and the other the "pupil" stop. FIG. 1 is a schematic of a simple microscope which illustrates this. The lens in FIG. 1 is designed to satisfy a condition referred to by designers of microscope systems as the "telecentric condition". A general understanding of the performance of a "telecentric" design is useful in understanding some of the key aspects of this invention.

In FIG. 1, a two dimensional object normal to axis 110 of lens 101, is located at field stop 100 which is positioned at the front focal point of lens 101. Object point 102 lies on the lens axis and is thus coincident with the front focal point of lens 101, while point 105 is displaced laterally some small distance from lens axis 110. At the same time, the lens exit pupil 103, is located at the back focal point 104 of lens 101. Object 100 can be thus expressed as a two dimensional distribution of intensity vs linear distance from the lens axis. This object is transformed into an intensity vs angular distribution after passing through lens 101. This same visualization can be used in the reverse direction. Exit pupil 103 can be described as an object located in the back focal plane 103 with an intensity vs linear distance dimensional distribution, which after passing in a reverse direction through lens 101 is transformed into an intensity vs angular distribution.

The unique aspect of a telecentric design is that each discreet point in the field is transformed into a collimated ray bundle with a discreet trajectory in the space of the exit pupil. Conversely each discreet point in the exit pupil is transformed into a collimated ray bundle with a discreet trajectories in the space of the field. Thus in FIG. 1, rays 106 and 107 which are diverging from field point 105, are parallel to each other upon leaving lens 101. Similarly, rays 108 and 109 which are diverging from field point 102, are parallel to each other upon leaving lens 101, but at a slight angle relative to the parallel rays which came from point 105. In the same sense in the reverse path, rays 106 and 107 which diverge slightly from pupil point 111 are traveling parallel to each other as they leave lens 101.

Figure 2:
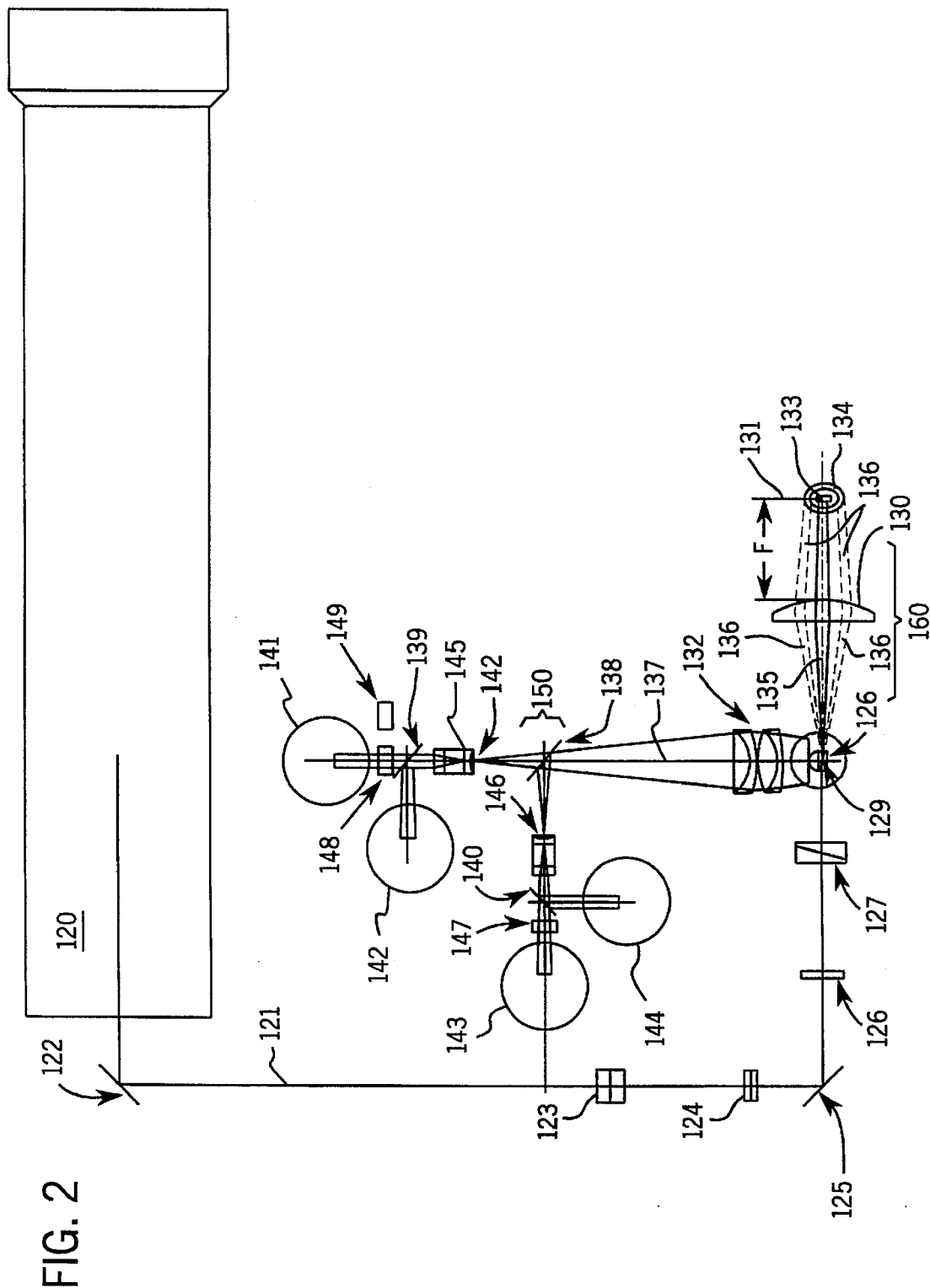
FIG. 2 is an optical plan view layout of a preferred embodiment of the invention.

FIG. 2 is an optical plan view layout of a preferred embodiment of the invention. Beam 121 from laser 120 is directed to flowcell 128 by means of mirrors 122 and 125, beam shaping lenses 123 and 124, focusing lens 126, and a vernier fine adjust element 127. The direction of flow of sample stream 129 is normal to the plane of the Figure. In a preferred embodiment, a side angle optical collection system 150 consists of a compound condenser lens 132 which collects scattered and fluorescence light from particles within sample stream 129, and directs this light 133 to photomultiplier detectors 141, 142, 143. In the preferred embodiment, lens 132 is a 9.0 mm focal length which is optically coupled to the flowcell with a resulting numeric aperture of 1.2. Dichroic beam splitters 134, 135, and 136 function to spectrally partition the optical beam 133 as is appropriate for each detector. Optical filters such as illustrated by 147, 148, and 149 are inserted automatically as required by the particular test protocol. It should be understood that the paths which are folded by means of dichroic beam splitters 138, 139, and 140, are optically the equivalent to the unfolded beam, and for the sake of clarity, the principals of the side angle optical collection system 150 is more simply understood by referring to the thin lens equivalent schematic of FIG. 4.

Figure 4:
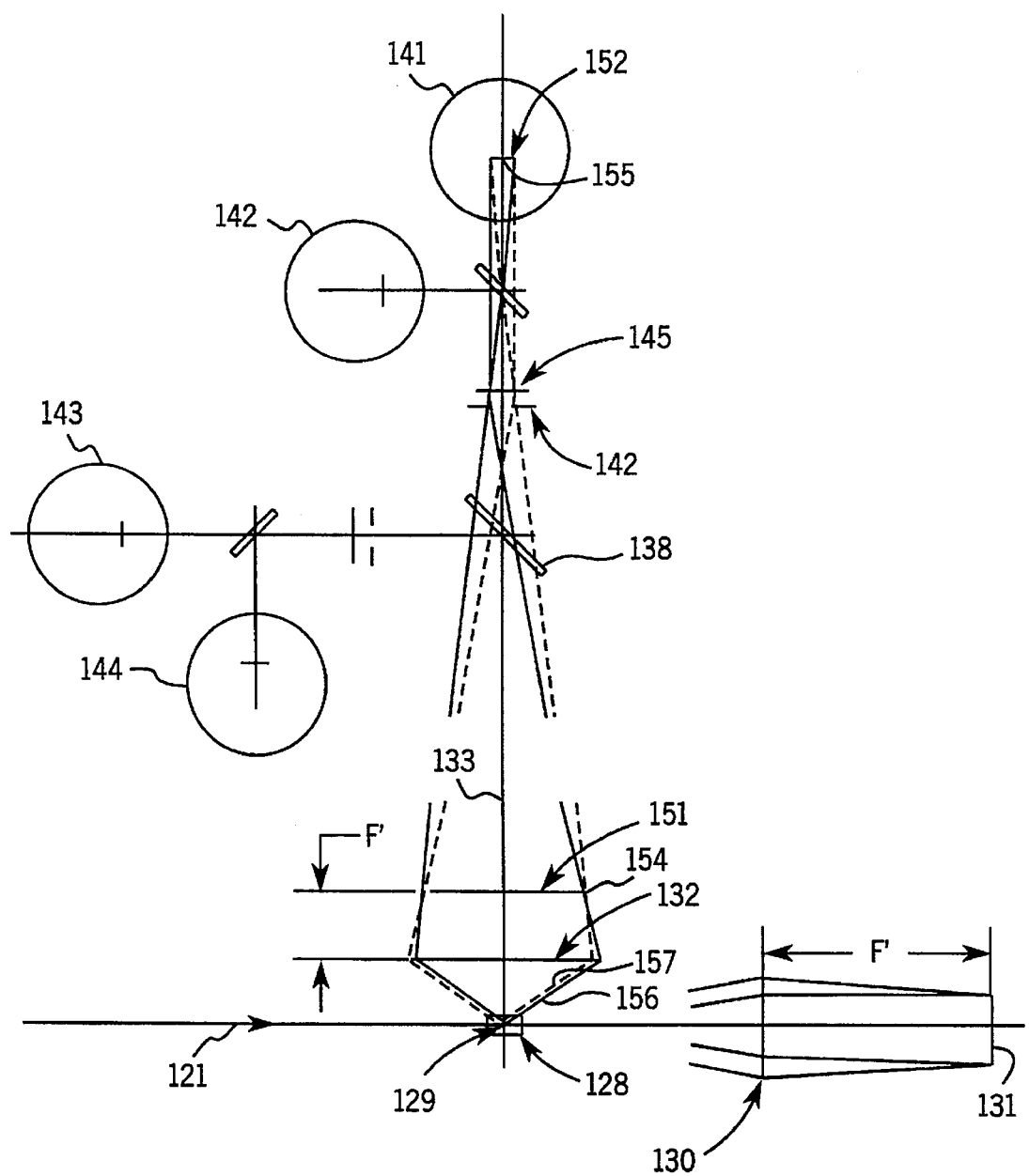
FIG. 4 is a thin lens equivalent schematic illustrating the principals of the side angle optical collection system of the present invention.

In FIG. 4 the compound lenses with curvature, thickness, and air spaces, are replaced with thin lens equivalents, which enables a clearer understanding of the imaging properties of the invention. Exit pupil 151 of condenser 132 is located in the back focal plane of condenser 132. Further, an image of exit pupil 151 is conjugate with the nominal photosensitive surface 152 of detector 141. Note that point 155 at detector photosensitive surface 152, is conjugate with point 154 at the outer edge of exit pupil 151, and that because of the telecentric nature of the design, the rays emanating within the flowcell which pass through these points, 156 and 157 are mutually parallel in the laser/flowcell space. This combination assures that all rays arriving at a given point at the detector correspond to a particular scatter angle relative to the laser, independent of where the particle is located within the flowcell. Thus the C.V. of particles within the flowcell is substantially independent of location within the stream, stream location within the flowcell, or spectral sensitivity of the photodetective surfaces.

An additional feature of side angle collection system 150 is that an image of the stream is placed at external aperture 142 which is located very near field lens 145. Aperture 142 functions to limit excess background light from the detectors, however it's size is not critical, and thus it is sized to be large enough to prohibit any sample light from being vignetted in cases where the stream image at the aperture is defocused due to stream wander along the beam axis 133 of the side angle collection system. This system overcomes the usual problem of the requirement to realign the side angle optical path whenever a flowcell or nozzle problem occurs. Additionally, the system intrinsically assures consistent angular integrity of the scattering particles relative to the laser illumination source.

Forward angle collection system 160, is also illustrated in FIGS. 2 and 4. Photodiode detector 131 is placed in the back focal plane of lens 130. FIG. 4 again illustrates the principal that all rays arriving at a discreet point on the detector emanate from the flowcell with a specific angular trajectory. In the reverse path sense, points in the detector space correspond to collimated rays in the flowcell space. In the preferred embodiment, detector 131 is an array detector in which the dimensional extent of each array element becomes the exit pupil of forward angle collecting lens 130.

Thus, so long as lens 130 and detector 131 are properly aligned with respect to each other, outer element 134 which is a circular ring with inner diameter 3.6 mm and outer diameter of 12.3 mm, will accept only scattered light from the flowcell with a range of scattering angles between 3 and 10 degrees relative to the laser axis. This signal is referred to as Intermediate Angle Scatter (IAS). Inner element 133 is rectangular in shape to match the beam divergence of the laser in the flowcell space. In the preferred embodiment the dimensions of element 133 are 1.5 mm×0.4 mm which corresponds to the vertical beam divergence of 37 mrad, and a horizontal divergence of 9.7 mrad. The equation which relates the pupil radial dimension to the angular divergence is:

$$Y = F \phi$$

where $Y$ is the radial dimension at the pupil, and $\phi$ is the scattering angle relative to the laser axis.

Inner element 133 detects a signal generally related to particle size, which is referred to as Axial Light Loss (ALL). In the ALL system, detector 133 collects only light within an incident cone of laser illumination. The signal of interest is a negative signal subtracted from the steady state laser signal.

From an alignment perspective this configuration of forward angle collection optics is a substantial simplification over prior art. The usual requirement that the forward angle system be precisely collinear with the side angle system, the stream, and the laser, is unnecessary. Additionally, the usual beam blocking and corresponding adjustment is not required, since the laser signal is used instead of blocked. Finally, once the proper positional relationship has been established between lens 130 and detector 131, the alignment, due to the back pupil aspect, is simply to adjust the detector for maximum steady state signal in the absence of any particle in the sensing zone. Thus, the telecentric aspect of this design in combination with the laser ALL measurement assures the absolute angular integrity of detector 131, and the lithographic process establishes the relative integrity of array 134 and 133.

In FIG. 3, the laser is brought into maximum coincidence with the stream by means of fine adjust mechanism 127. This consists of a pair of wedge prisms located between laser focusing lens 126 and flowcell 128. The wedge prisms are positioned so that change in the air space laterally displaces the laser beam in flowcell 128 without any change in the illumination angles. The mechanism is extremely easy to control in order to accommodate micron beam displacements in the flowcell for maximum signal sensitivity. Since the adjustment is lateral rather than angular, the alignment of the forward angle collection system 160 as well as side scatter system 150 remain unaffected is affected.

While certain representative embodiments and details have been shown for the purpose of illustrating the invention, various changes and modifications can be made herein without departing from the essence and scope of the invention defined in the claims.

We claim:

1. A flow cytometric optical system for the simultaneous detection of several characteristics of particles suspended in a flowing medium comprising:

a flowcell through which the particles pass substantially one particle at a time;

a light directing optical system for directing light from a light source onto the flowing particles in the flowcell;

a side angle optical collection system for receiving light from the flowing particles, and for directing the light to one or more of a first set of detectors;

a forward angle collection system for receiving light from the flowing particles, and for directingthe light to one or more of a second set of detectors;

wherein the side angle optical collection system comprises a condenser lens for directing light toward the first set of detectors, an exit pupil of the condenser lens located at the back focal plane of the condenser lens, and a photosensitive surface of one or more of the first set of detectors located at conjugate points of the back focal plane of the condenser lens such that an image of the exit pupil is positioned at the photosensitive surface of the one or more of the first set of detectors; and wherein the forward angle optical collection system comprises a collecting lens for directing light toward the second set of detectors, wherein the collecting lens exit pupil located in the back focal plane of the collecting lens, a photosensitive surface of one or more of the second set of detectors located at the back focal plane of the collecting lens.

2. The optical system of claim 1 wherein the light source is a laser.

3. The optical system of claim 2 wherein the second set of detectors comprises an array detector comprising two or more elements, each element defining an angular acceptance range of light scattered by the particles as determined by the radial linear limiting dimensions of that element.

4. The optical system of claim 3 wherein one element of the array detector has physical sensitivity dimensions corresponding to the laser beam divergence within the flowcell in the absence of any particles.

5. The optical system of claim 2 wherein the laser has a focal waist focused within the flowcell.

6. The optical system of claim 2 wherein the light directing optical system comprises a fine adjust element to enable a lateral translation or the laser beam within the flowcell without adversely effecting the trajectory of the incident laser beam.

7. The optical system of claim 6 wherein the fine adjust element comprises a pair of wedge prisms, separated by an adjustable air space, the pair of prisms located between a laser focusing lens and the flowcell.

8. The optical system of claim 1 wherein the first set of detectors comprises one or more photomultipler tubes.

9. The optical system of claim 1 wherein the condenser lens is a compound lens.

10. The optical system of claim 9 wherein the exit pupil of the compound condenser lens is virtual and located within the lens.

11. The optical system of claim 1 wherein the second set of detectors comprises one or more photodiodes.

12. The optical system of claim 1 wherein the second set of detectors comprises a single silicon photodiode with an angular acceptance range of the light scattered from the particles is determined by the linear dimensions of the photosensitive surface of the photodiode.

13. The optical system of claim 1 wherein the condenser lens forms at least one image of the flowcell medium/particle stream at a position located between the condenser and the first set of detectors.

14. The optical system of claim 13 wherein the side angle optical system further comprises at least one aperture located at the at least one flowcell medium/particle stream image, the aperture limiting light to the one or more of the first set of detectors.

15. The optical system of claim 14 wherein the dimensions of the aperture are greater than the dimensions of the flowcell medium/particle stream such that the defocusing effects of stream wander within the flowcell, flowcell replacement or the replacement of the medium/particle stream forming means does not adversely affect the signal received at a detector.

16. The optical system of claim 14 wherein the side angle optical collection system further comprises a field lens located at or near the aperture, the field lens producing an image of the condenser exit pupil at the photosensitive surface of at least one of the first set of detectors.

17. The optical flowcell of claim 1 wherein the field lens comprises a compound lens.

18. A flow cytometric optical system for the simultaneous detection of several characteristics of particles suspended in a flowing medium comprising:

a flowcell through which the particles pass;

an optical system for directing light from a light source onto the flowing particles in the flowcell;

a side angle optical collection system for receiving light from the flowing particles, and for directing the light to one or more of a first set of detectors;

a forward angle collection system for receiving light from the flowing particles, and for directing said light to one or more of a second set of detectors;

wherein the side angle optical collection system comprises a condenser lens for directing light toward the first set of detectors, an exit pupil of said condenser lens located at the back focal plane of said condenser lens, and a photosensitive surface of one or more of said first set of detectors being located at conjugate points of the back focal plane of said condenser lens, such that an image of said exit pupil is positioned at the photosensitive surface of one or more of the first set of detectors; and wherein the forward angle optical collection system comprises a collecting lens for directing light toward the second set of detectors, an exit pupil of the collecting lens located in the back focal plane of the collecting lens, and a photosensitive surface of one or more of the second set of detectors being located at conjugate points of the back focal plane of said collecting lens, such that an image of said exit pupil is located at the photosensitive surface of one or more of the second set of detectors.

19. The optical system of claim 18 wherein the light source is a laser.

20. The optical system of claim 19 wherein the second set of detectors comprises an array detector comprising two or more elements, each element defining an angular acceptance range of light scattered by the particles as determined by the radial linear limiting dimensions of that element.

21. The optical system of claim 20 wherein one element of the array detector has physical sensitivity dimensions corresponding to the laser beam divergence within the flowcell in the absence of any particles.

22. The optical system of claim 19 wherein the laser has a focal waist focused within the flowcell.

23. The optical system of claim 19 wherein the light directing optical system comprises a fine adjust element to enable a lateral translation or the laser beam within the flowcell without adversely effecting the trajectory of the incident laser beam.

24. The optical system of claim 23 wherein the fine adjust element comprises a pair of wedge prisms, separated by an adjustable air space, the pair of prisms located between a laser focusing lens and the flowcell.

25. The optical system of claim 18 wherein the first set of detectors comprises one or more photomultipler tubes.

26. The optical system of claim 18 wherein the condenser lens is a compound lens.

27. The optical system of claim 26 wherein the exit pupil of the compound condenser lens is virtual and located within the lens.

28. The optical system of claim 18 wherein the second set of detectors comprises one or more photodiodes.

29. The optical system of claim 18 wherein the second set of detectors comprises a single silicon photodiode with an angular acceptance range of the light scattered from the particles as determined by the linear dimensions of the photosensitive surface of the photodiode.

30. The optical system of claim 18 wherein the condenser lens forms at least one image of the flowcell medium/ particle stream at a position located between the condenser and the first set of detectors.

31. The optical system of claim 30 wherein the side angle optical system further comprises at least one aperture located at the at least one flowcell medium/particle stream image, the aperture limiting light to the one or more of the first set of detectors.

32. The optical system of claim 31 wherein the dimensions of the aperture are greater than the dimensions of the flowcell medium/particle stream such that the defocusing effects of stream wander within the flowcell, flowcell replacement or the replacement of the medium/particle stream forming means does not adversely affect the signal received at a detector.

33. The optical system of claim 31 wherein the side angle optical collection system further comprises a field lens located at or near the aperture, the field lens producing an image of the condenser exit pupil at the photosensitive surface of at least one of the first set of detectors.

34. The optical flowcell of claim 18 wherein the field lens comprises a compound lens.

* * * * *

UNITED STATES PATENT AND TRADEMARK OFFICE
CERTIFICATE OF CORRECTION

PATENT NO. : 5,631,730
DATED : May 20, 1997
INVENTOR(S) : Chupp et al.

It is certified that error appears in the above-indentified patent and that said Letters Patent is hereby corrected as shown below:

Column 4, line 4, change "107" to --108--.

Column 5, line 58, delete "is affected".

Signed and Sealed this

Fourteenth Day of October, 1997

*Attest:*

BRUCE LEHMAN

*Attesting Officer*  *Commissioner of Patents and Trademarks*